United States Patent [19]
Nikiforov

[11] Patent Number: 6,107,044
[45] Date of Patent: Aug. 22, 2000

[54] APPARATUS AND METHODS FOR SEQUENCING NUCLEIC ACIDS IN MICROFLUIDIC SYSTEMS

[75] Inventor: Theo T. Nikiforov, Campbell, Calif.

[73] Assignee: Caliper Technologies Corp., Mountain View, Calif.

[21] Appl. No.: 09/334,527

[22] Filed: Jun. 16, 1999

Related U.S. Application Data

[63] Continuation of application No. 08/953,005, Oct. 16, 1997, Pat. No. 5,958,694.

[51] Int. Cl.[7] ................................................ C12Q 1/68
[52] U.S. Cl. ............................................. 435/6; 210/198.2
[58] Field of Search ............................... 435/6; 210/198.2

[56] References Cited

U.S. PATENT DOCUMENTS

| | | |
|---|---|---|
| 4,390,403 | 6/1983 | Batchelder . |
| 4,711,955 | 12/1987 | Ward et al. . |
| 4,908,112 | 3/1990 | Pace . |
| 5,126,021 | 6/1992 | Grossman . |
| 5,126,022 | 6/1992 | Soane et al. . |
| 5,164,055 | 11/1992 | Dubrow . |
| 5,171,534 | 12/1992 | Smith . |
| 5,181,999 | 1/1993 | Wiktorowicz . |
| 5,187,085 | 2/1993 | Lee . |
| 5,188,934 | 2/1993 | Menchen et al. . |
| 5,264,101 | 11/1993 | Demorest et al. . |
| 5,290,418 | 3/1994 | Menchen et al. . |
| 5,366,860 | 11/1994 | Bergot et al. . |
| 5,374,527 | 12/1994 | Grossman . |
| 5,468,365 | 11/1995 | Menchen et al. . |
| 5,498,392 | 3/1996 | Wilding et al. . |
| 5,512,131 | 4/1996 | Kumar et al. . |
| 5,552,028 | 9/1996 | Madabhushi et al. . |
| 5,567,292 | 10/1996 | Madabhushi et al. . |
| 5,571,410 | 11/1996 | Swedberg et al. . |
| 5,585,069 | 12/1996 | Zanzucchi et al. . |
| 5,593,838 | 1/1997 | Zanzucchi et al. . |
| 5,603,351 | 2/1997 | Cherukuri et al. . |
| 5,635,358 | 6/1997 | Wilding et al. . |
| 5,637,469 | 6/1997 | Wilding et al. . |

FOREIGN PATENT DOCUMENTS

| | | |
|---|---|---|
| WO 9604547 | 2/1996 | WIPO . |
| WO 9702357 | 1/1997 | WIPO . |
| WO 9712063 | 4/1997 | WIPO . |

OTHER PUBLICATIONS

Celi, F.S. et al., "A rapid and versatile method to synthesize internal standards for competitive PCR," *Nucl. Acids Res.* 21(4):1047 (1993).

Dasgupta, P.K. et al., "Electroosmosis: A Reliable Fluid Propulsion System for Flow Injection Analysis," *Anal. Chem.* 66:1792–1798 (1994).

Effenhauser, C.S. et al., "High–Speed Separation of Anti-sense Oligonucleotides on a Micromachined Capillary Electrophoresis Device," *Anal. Chem.* 66:2949–29953 (1994).

Jacobson, S.C. et al., "Fused Quartz Substrates for Microchip Electrophoresis," *Anal. Chem.* 67:2059–2063 (1995).

Manz, A. et al., "Electroosmotic pumping and electrophoretic separations for miniaturized chemical analysis systems," *J. Micromech. Microeng.* 4:257–265 (1994).

Porter et al., "Direct PCR sequencing with boronated nucleotides," *Nucl. Acids Res.* 25(8):1611–1617 (1997).

Ramsey, J.M. et al., "Microfabricated chemical measurement systems," *Nature Med.* 1:1093–1096 (1995).

Seiler, K. et al., "Planar Glass Chips for Capillary Electrophoresis: Repetitive Sample Injection, Quantitation, and Separation Efficiency," *Anal. Chem.* 65:1481–1488 (1993).

Seiler, K. et al., "Electroosmotic Pumping and Valveless Control of Fluid Flow Within a Manifold of Capillaries on a Glass Chip," *Anal. Chem.* 66:3485–3491 (1994).

*Primary Examiner*—Scott W. Houtteman
*Attorney, Agent, or Firm*—Matthew B. Murphy

[57] ABSTRACT

The present invention is generally directed to microfluidic systems and methods of using such systems in the determination of the nucleotide sequence of target nucleic acid sequences (referred to herein as the "target"). In particular, the present invention provides methods and systems for determining the relative positions within a target nucleic acid sequence that are occupied by a given nucleotide, e.g., A, T, G or C, by separating mixtures of nested sets of fragments of the target nucleic acid, which sets each include fragments that terminate in a different given nucleotide.

26 Claims, 5 Drawing Sheets

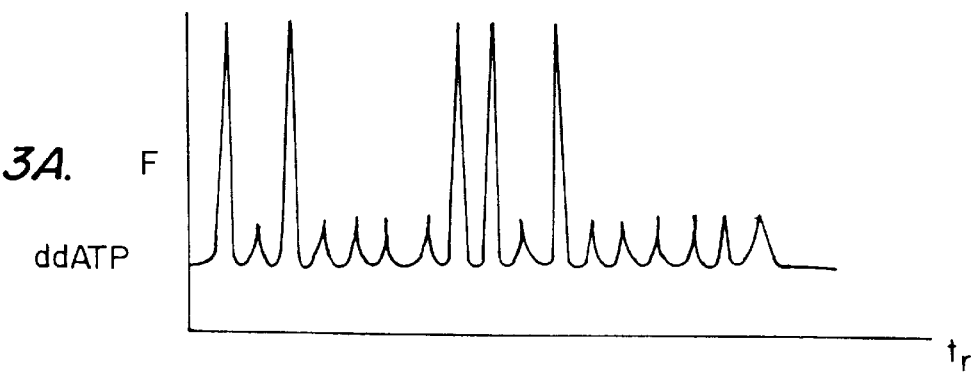
FIG. 3A. ddATP
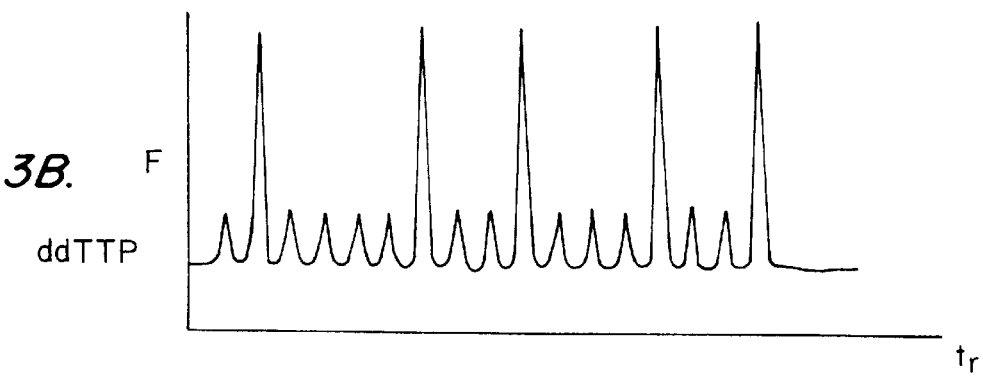
FIG. 3B. ddTTP
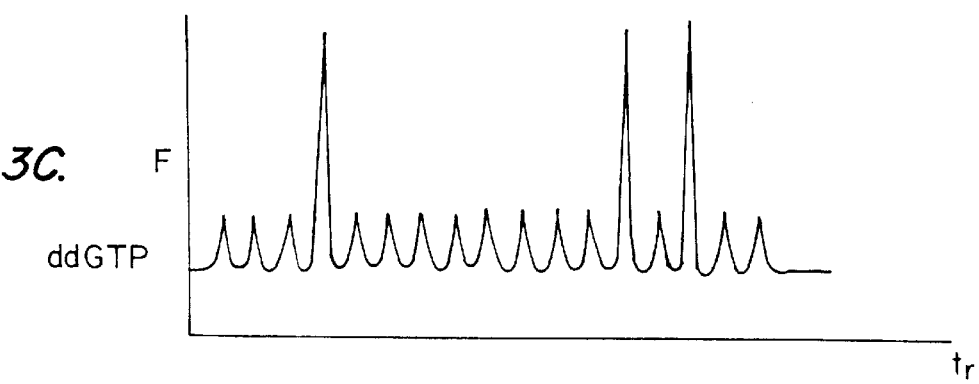
FIG. 3C. ddGTP
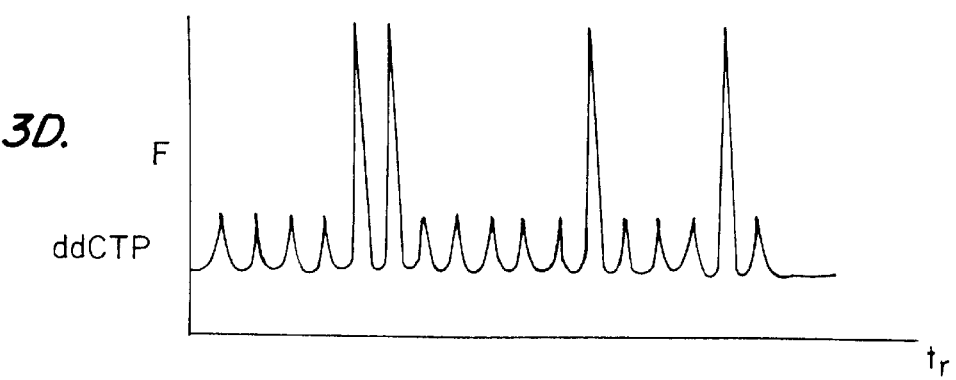
FIG. 3D. ddCTP

APPARATUS AND METHODS FOR SEQUENCING NUCLEIC ACIDS IN MICROFLUIDIC SYSTEMS

CROSS-REFERENCE TO RELATED APPLICATION

This application is a continuation of U.S. patent application Ser. No. 08/953,005, filed Oct. 16, 1997) now U.S. Pat. No. 5,958,694, the full disclosure of which is incorporated herein by reference in its entirety.

BACKGROUND OF THE INVENTION

The basic foundation of life is built around the transmission of information, whether from cell to cell or from generation to generation. The transmission of this information is carried out by fundamental building blocks of biological organisms including proteins, nucleic acids and the like. Accordingly, attempts to understand biological processes, variations in those processes and effectors of those processes, have naturally focused upon these building blocks to provide the information necessary for that understanding.

In the field of nucleic acid analysis, there have been developed a number of methods and systems for determining the sequence of nucleotides in a given nucleic acid polymer. For example, in the 1970s, Maxam and Gilbert developed a method of sequencing nucleic acid polymers by the selective chemical cleavage of the overall polymer. Maxam and Gilbert, Proc. Nat'l Acad. Sci., 74:560–564 (1977). Specifically, labeled nucleic acids were preferentially and partially cleaved after one of the four nucleotides to create a nested set of fragments terminating in the particular nucleotide. Different conditions are applied to cleave after each of the four nucleotides creating corresponding nested sets. The fragments produced from the four different treatments were then separated in four different lanes on a conventional polyacrylamide slab gel. Reading the bands on the gel in ascending order, one essentially reads off the sequence of the nucleic acid.

A reverse approach was presented by Sanger et al., Proc. Nat'l Acad. Sci., 74:5463–5467 (1977), where the four nested sets of fragments of the nucleic acid polymer were produced by transcription in the presence one of four chain terminating dideoxynucleotide analogs. In particular, transcription of a nucleic acid template strand in the presence of the four deoxynucleoside triphosphates (dNTPs) and one dideoxynucleoside triphosphate analog (ddNTP) results in the production of a nested set of fragments terminating in the one ddNTP. Specifically, during transcription, the occasional incorporation of the ddNTP into the sequence terminates the transcription process at that nucleotide. This process is repeated with each of the four different ddNTP analogs.

While these methods have proven effective in determining sequence information, the use of slab gels and the reading processes are laborious and time consuming. Smith et al., U.S. Pat. No. 5,171,534, reports the use of four dideoxynucleotide analogs in sequencing operations, wherein each different dideoxynucleotide is labeled with a spectrally distinguishable fluorescent moiety, in the method of Sanger, above. The four nested sets are produced using these dideoxynucleotides, whereupon each set bears a spectrally resolvable label. All four sets are then sized in a single pass through a gel filled capillary, permitting the separation of the fragments based upon size. Fragments from each set are then distinguished of from one another by virtue of filtering optics specific for the emission spectra of each resolvable label.

Again, while the use of differently labeled nested fragment sets provides advantages over previously used systems, sequencing by these methods still requires a substantial amount of labor, as well as substantial expense in purchasing the necessary equipment, e.g. separations and detection equipment. Further, different fluorescent labels typically have different excitation spectra. As such, use of a single excitation light source in exciting and detecting all of four different labels, e.g., in the method of Smith et al., results in less than optimal quantum yields for each of the labels used. Specifically, the excitation light source is typically not optimized for all of the fluorescent groups.

The present invention, on the other hand, provides a substantially low cost method and system for sequencing nucleic acids, which system is readily automatable and integratable with upstream or downstream processes.

SUMMARY OF THE INVENTION

The present invention generally provides microfluidic devices and systems, as well as methods of using such devices and systems in the determination of the nucleotide sequences in target nucleic acids.

In a first aspect, the present invention provides a microfluidic system for determining relative positions in a target nucleic acid sequence that are occupied by a given nucleotide. The system comprises a microscale separation channel having first and second ends for separating nucleic acid fragments by size. The system also comprises a first source of a first nested set of fragments of the target nucleic acid sequence, in fluid communication with the separation channel, where each of the fragments in the first nested set terminates at a different position occupied by the given nucleotide. Also included is a second source of a second nested set of fragments of the target nucleic acid sequence in fluid communication with the separation channel, where each of the fragments in the second nested set terminates in a nucleotide different from the given nucleotide. The system also comprises a means for mixing a first concentration of the first nested set with a second concentration of the second nested set in a first mixture, where the first concentration being determinably different from the second concentration. Further, the system comprises a means for injecting a portion of the first mixture into the separation channel and transporting the portion through the separation channel to separate the fragments from the nested sets. Also included is a detector for detecting the separate fragments of the first and second nested sets in the separation channel. In preferred aspects, the transport of materials, e.g., nested sets of fragments, through the various channels is carried out using a controlled electrokinetic material transport system.

In another preferred aspect, the sources of the nested sets of fragments are integrated into a single body structure with the microscale channels of the microfluidic device or system.

In a related aspect, the present invention provides a method of determining positions in a target nucleic acid sequence occupied by a first nucleotide. The method comprises providing a microfluidic device according to the present invention. A first concentration of the first nested set from the first source is mixed with a second concentration of the second nested set from the second source to form a first mixture, wherein the first and second concentrations being distinguishably different relative to each other. A portion of the first mixture is transported through the separation channel to separate the fragments in each of the first and second nested sets. The fragments separated in the transporting step are detected and the fragments from the first nested set are distinguished from fragments from the second nested set based upon their relative concentration. The relative position within the target nucleic acid sequence occupied by the first nucleotide is then determined by comparing the size of fragments in the first nested set relative to the size of fragments in the second nested set.

BRIEF DESCRIPTION OF THE FIGURES

FIG. 3A–D illustrate comparative plots of fluorescent signal vs. time for fragments separated in the separation portion of the microfluidic device of FIG. 2.

DETAILED DESCRIPTION OF THE INVENTION

Figure 1:
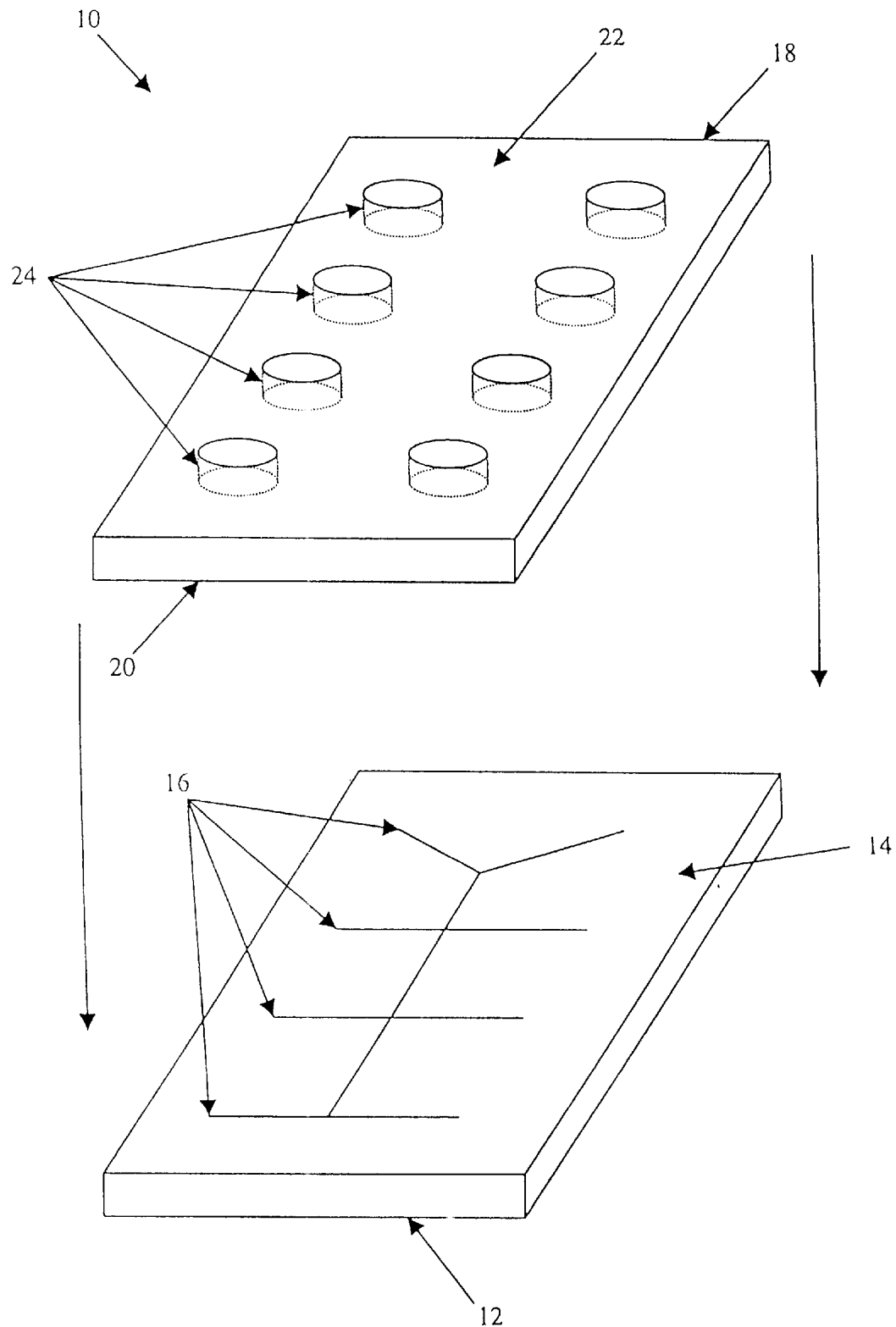
FIG. 1 schematically illustrates the body structure and assembly of a microfluidic device incorporating a layered body structure.

The present invention is generally directed to microfluidic systems and methods of using such systems in the determination of the nucleotide sequence of target nucleic acid sequences (referred to herein as the "target"). In particular, the present invention provides methods and systems for determining the relative positions within a target nucleic acid sequence that are occupied by a given nucleotide, e.g., A, T, G or C. As used herein, the phrase "target nucleic acid sequence" is used to describe a nucleic acid polymer for which the sequence of nucleotide monomers is sought. The target nucleic acid may include natural or unnatural nucleic acid monomers, DNA, RNA or derivatives thereof. In general, the methods and systems of the present invention employ selected mixtures of nested sets of fragments of the target nucleic acid that is to be sequenced. Separation of these fragments by size and comparison of their relative concentrations permits the elucidation of the relative positions of specific nucleotides within the overall target sequence.

As noted, the above-described sequencing methods are carried out within microfluidic devices or systems. As used herein, the term "microscale" or "microfabricated" generally refers to structural elements or features of a device which have at least one fabricated dimension in the range of from about 0.1 $\mu$m to about 500 $\mu$m. Thus, a device referred to as being microfabricated or microscale will include at least one structural element or feature having such a dimension. When used to describe a fluidic element, such as a passage, chamber or conduit, the terms "microscale," "microfabricated" or "microfluidic" generally refer to one or more fluid passages, chambers or conduits which have at least one internal cross-sectional dimension, e.g., depth, width, length, diameter, etc., that is less than 500 $\mu$m, and typically between about 0.1 $\mu$m and about 500 $\mu$m. In the devices of the present invention, the microscale channels or chambers preferably have at least one cross-sectional dimension between about 0.1 $\mu$m and 200 $\mu$m, more preferably between about 0.1 $\mu$m and 100 $\mu$m, and often between about 0.1 $\mu$m and 20 $\mu$m. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby at least two channels are in fluid communication.

The body structure of the microfluidic devices described herein typically comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device.

FIG. 1 illustrates an example of a two-layer body structure 10, for a microfluidic device. In preferred aspects, the bottom portion of the device 12 comprises a solid substrate that is substantially planar in structure, and which has at least one substantially flat upper surface 14. A variety of substrate materials may be employed as the bottom portion. Typically, because the devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, e.g., silicon, it will often be desirable to provide an insulating coating or layer, e.g., silicon oxide, over the substrate material, and particularly in those applications where electric fields are to be applied to the device or its contents.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. patent application Ser. No. 08/843,212, filed Apr. 14, 1997, and which is incorporated herein by reference in its entirety for all purposes.

The channels and/or chambers of the microfluidic devices are typically fabricated into the upper surface of the bottom substrate or portion 12, or the lower surface 20 of upper substrate 18, or a combination thereof, as microscale grooves or indentations 16, using the above described microfabrication techniques. The top portion or substrate 18 also comprises a first planar surface 20, and a second surface 22 opposite the first planar surface 20. In the microfluidic devices prepared in accordance with the methods described herein, the top portion also includes a plurality of apertures, holes or ports 24 disposed therethrough, e.g., from the first planar surface 20 to the second surface 22 opposite the first planar surface.

The first planar surface 20 of the top substrate 18 is then mated, e.g., placed into contact with, and bonded to the planar surface 14 of the bottom substrate 12, covering and sealing the grooves and/or indentations 16 in the surface of the bottom substrate, to form the channels and/or chambers (i.e., the interior portion) of the device at the interface of these two components. Methods for bonding of substrates vary depending upon the make-up of the substrate. For example, thermal bonding techniques are typically utilized for silica-based substrates, where the mated substrates are heated to temperatures in the range of from 500 to 1200° C. Alternatively, or in the case of polymeric substrates, adhesives may be used to bond the mated substrates together. Polymeric substrates may also be bonded using sonic welding techniques, as well as more mild thermal techniques, e.g., bonding under temperatures in the range of 100 to 200° C.

The holes 24 in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device.

In many embodiments, the microfluidic devices will include an optical detection window disposed across one or more channels and/or chambers of the device. Optical detection windows are typically transparent such that they are capable of transmitting an optical signal from the channel/chamber over which they are disposed. Optical detection windows may merely be a region of a transparent cover layer, e.g., where the cover layer is glass or quartz, or a transparent polymer material, e.g., PMMA, polycarbonate, etc. Alternatively, where opaque substrates are used in manufacturing the devices, transparent detection windows fabricated from the above materials may be separately manufactured into the device.

The microfluidic devices for use with the methods described herein, typically comprise a body structure, as described above, which includes a separation channel or column disposed therein, for separating nucleic acid sequences by size. In order to optimize separation of nucleic acid molecules, the separation channel generally includes an appropriate separation matrix disposed therein. Typically, such separation matrices include a high molecular weight polymer solution, e.g., between about 5 and 200 Kd, which polymer bears an appropriate charge to nullify or significantly reduce any charge on the wall surface of the separation channel, which can result in excessive electroosmotic flow within the separation channel. Typically, the separation matrix will include an acrylamide polymer, hydroxymethyl cellulose, or agarose. In preferred aspects, the matrix includes a methylacrylamide polymer and more particularly, a dimethylacrylamide polymer. Examples of such polymers include, e.g., the polymers described in U.S. Pat. Nos. 5,126,021, 5,164,055, 5,181,999, 5,264,101, 5,290,418, 5,374,527, 5,468,365, 5,552,028, and 5,567,292, all of which are incorporated herein by reference. Such polymers are generally commercially available, e.g., from Perkin-Elmer/Applied Biosystems, Inc.

The separation matrix or polymer is typically introduced into the channels of the microfluidic device by placing the polymer solution in one well of the device and allowing capillary action to draw the polymer through the channels of the device. Slight pressure is optionally added to ensure adequate filling of the channels.

The microfluidic devices and systems for use in accordance with the methods described herein, also include a source of a solution containing a first nested set of fragments of the target nucleic acid sequence and at least a source of a solution containing a second nested set of fragments of the target nucleic acid sequence. Optionally, the devices and systems will include separate sources of third and fourth nested sets of fragments. Each of these fragment sources is in fluid communication with the microscale separation channel. In preferred aspects, these fragment sources are in fluid communication with the separation channel via a common injection channel, where the injection channel intersects the separation channel. Typically, the sources of fragments of the target are integrated into the body structure of the microfluidic device, as a reservoir or port disposed through the body from the exterior to the interior portion, e.g., as described above.

The first nested set of fragments of the target nucleic acid sequence comprises a plurality of different fragments of the target, where each fragment terminates in a given or selected nucleotide, e.g., A, T, G or C or analogs thereof, i.e., ddNTPs, labeled ddNTPs, and boronated NTPs and labeled boronated NTPs. For example, a first fragment in the first nested set comprises a portion of the target and terminates at a particular position within the target that is occupied by an A. A second fragment includes the entire first fragment, but extends to the next position in the sequence occupied by an A, at which point the fragment terminates. The second nested set of fragments comprises a plurality of fragments where each fragment terminates in a nucleotide or nucleotide analog that is different from the terminating nucleotide of the first set. In particular, assuming the first nested set includes the nested set of fragments that terminate in A, then the second nested set includes the fragments terminating in T, G and/or C. Optionally, sources of third and fourth nested sets of fragments are provided, e.g., in their appropriate reservoirs, in fluid communication with the injection channel. In this instance, the second nested set of fragments includes fragments that terminate in a nucleotide different from the first nested set, the third nested set of fragments includes fragments that terminate in a nucleotide different from the first and second nested sets, and the fourth nested set of fragments terminates includes fragments that terminate in a nucleotide different from the first, second and third sets. In terms of the example provided above, the second set of fragments would terminate in T, while the third and fourth sets terminate in G and C, respectively.

The solutions containing the nested sets of fragments of the target sequence, as described above, are typically prepared according to known methods, see Sanger et al., supra, and Porter et al., Nucleic Acids Res. 25(8):1611–1617. Alternatively, the Maxam and Gilbert methods may be employed. In the latter instance, the nested sets may terminate in a nucleotide immediately adjacent to the selected nucleotide. This is a result of cleaving away the nucleotide of interest during the cleavage process, i.e., when sequencing in the 5' to 3' direction where the 5' terminus is labeled, the nucleotide of interest may remain with the unlabeled 3' fragment, and thus, not be subject to detection. By immediately adjacent is meant a nucleotide that is in the adjacent position to the nucleotide of interest (the selected nucleotide).

A selected mixture of fragments from each of the nested sets is prepared such that one nested set of fragments is at a concentration that is detectably different from the other fragment sets present in the mixture. This is also termed an "offset concentration." By a "detectably different concentration," is generally meant that upon detection, e.g., following separation, fragments of one nested set will produce a signal intensity that is statistically different, either higher or lower, than the signal intensity produced by fragments from the other nested sets or sets. Typically, the detectably different concentration will yield a signal intensity that is greater than a factor of 2 different from the signal of any of the other nested sets, e.g., less than half the signal or greater than twice the signal. Preferably, the detectably different concentration will be greater than a factor of greater than at least 3, more preferably at least 4, still more preferably, greater than at least 5, and in many cases, a factor of greater than at least 10 different from the signal of any of the other nested sets, e.g., less than one tenth the signal or greater than five times the signal, and more preferably, greater than a factor of 10 different from the other signals, e.g., less than one tenth or greater than ten times the signal intensity from the other nested sets.

A portion of the selected mixture is then injected into the separation channel and the various fragments present therein are separated and detected. Because one nested set is injected at a detectably different, e.g., greater, concentration than the other nested sets, the separated fragments from this set produce detectably different, e.g., larger, signal peaks from those of the other fragments, permitting their ready identification. Further, as the overall mixture represents the nested set of fragments of the target, i.e., representing each single nucleotide extension, comparison of the elution profile, or relative molecular weight, of the larger signal peaks with the smaller peaks allows a determination of the positions in the overall target sequence that are occupied by the nucleotide that is at the terminus of the fragments in the first nested set. Thus, the smaller peaks function as a single nucleotide sizing ladder or internal standard for ordering the fragments from the first nested set. This separation, detection and ordering is repeated with different selected mixtures of the various nested sets of fragments, so as to order the fragments from the other nested sets, and thereby determine the positions in the target sequence that are occupied by the terminal nucleotides of those fragments.

Although described in terms of performing three or four different separation, detection and ordering stages, it will be readily appreciated that fewer stages can be utilized. Specifically, the selected mixture of fragments optionally includes the various nested sets of fragments, where each set of fragments is present at a detectably different concentration than all other nested sets. Thus, within a selected mixture, the first nested set is present at a first concentration, while the second nested set is present at a second concentration that is detectably different from the first. The third nested set s present at a concentration that is detectably different from both the first and second sets, and the fourth nested set is present at yet a further different concentration, e.g., detectably different from the first, second, and third sets. Variations on this format are also embodied in the methods described herein, e.g., where two of the four nested sets have detectably different concentrations and two do not, thus reducing the total number of separation, detection and ordering stages required, i.e., from 4 to 2.

The devices and systems gain substantial ease of use and automatability through the use of controlled electrokinetic material transport systems. In brief, these systems controllably mix the various nested sets of fragments, transport the mixture to the separation channel, and inject a portion of that mixture into the separation channel to separate out the constituent fragments. "Electrokinetic material transport" refers to systems which transport and direct materials within an interconnected channel and/or chamber containing structure, through the application of electrical fields to the materials, thereby causing material movement through and among the channel and/or chambers, i.e., cations will move toward the negative electrode, while anions will move toward the positive electrode.

As used herein, the phrase "controlled electrokinetic transport" refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, to Ramsey, which is incorporated herein by reference in its entirety for all purposes. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner.

Although described for the purposes of illustration with respect to a four way, cross intersection, these controlled electrokinetic material transport systems can be readily adapted for more complex interconnected channel networks, e.g., arrays of interconnected parallel channels.

In the devices, systems and methods described herein, controlled electrokinetic transport permits the controlled transport of selected amounts of each of the nested sets into a central mixing area. The same electrokinetic transport system then transports the mixed sets to and injects the mixture into the separation channel. The use of such transport systems is particularly useful in light of the electrophoresis step used in the separation process. Such systems also require little operator input beyond the original programming, and are also readily automatable and integratable with other operations.

In addition to providing a facile and readily automatable method of determining the sequence of a target nucleic acid, the methods and systems described herein, also provide an internal verification system. Specifically, because numerous overlapping separation, detection and ordering stages are run to determine the relative ordering of all of the fragments from all of the nested sets, each successive stage becomes a verification of the prior stage, permitting more accurate ordering of the fragments from the various nested sets, and thus permitting more accurate identification of the nucleotide present at each position within the target sequence, also referred to as "base calling."

Figure 2:
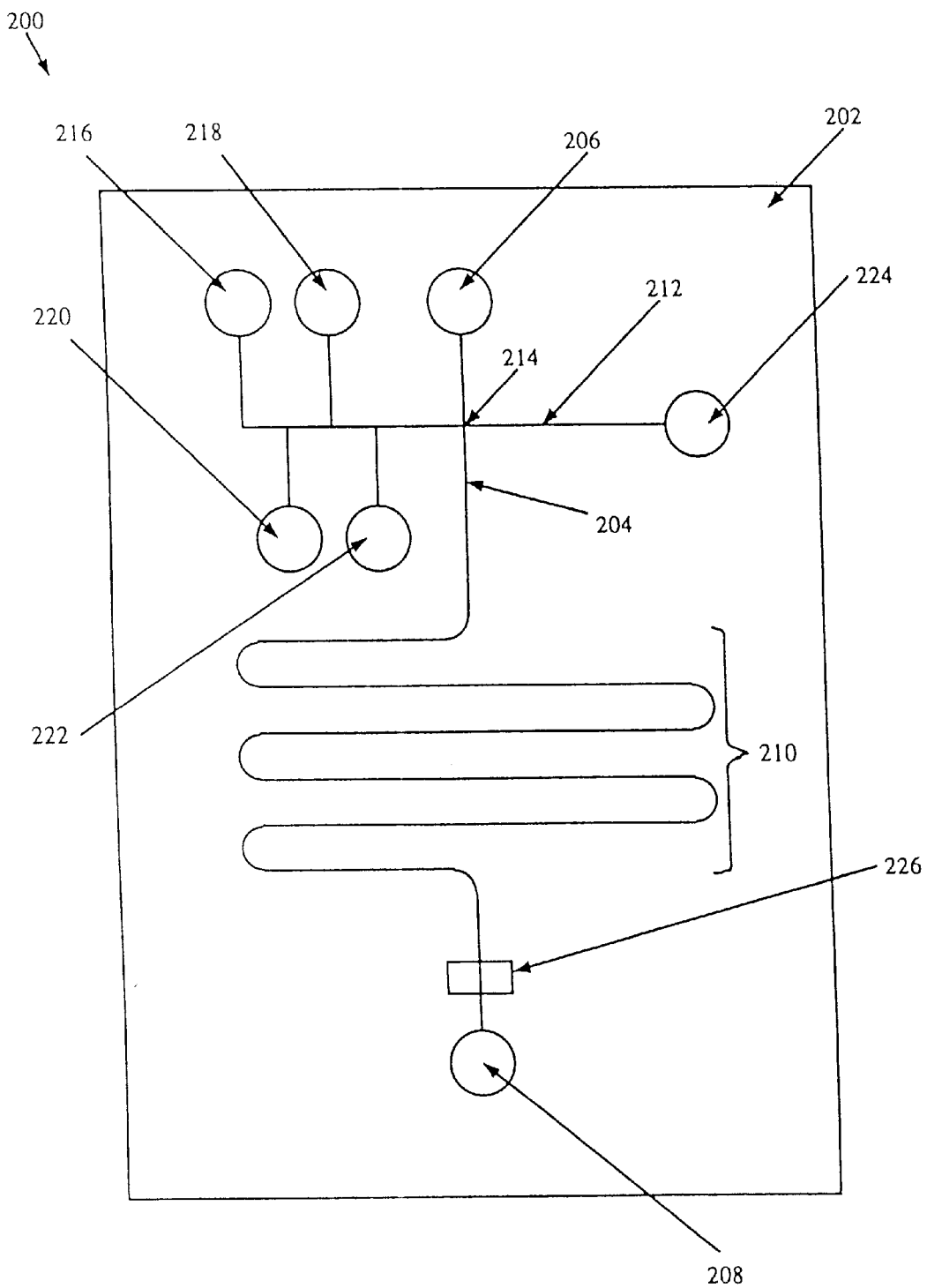
FIG. 2 schematically illustrates the channel and port/reservoir geometry for a microfluidic device that is useful in performing sequencing operations.

A schematic illustration of an integrated microfluidic device according to the present invention is illustrated in FIG. 2. As shown, the microfluidic device 200 includes a planar body structure 202, typically fabricated from at last two mated, planar substrates, as shown in FIG. 1. Disposed within body structure 202 is a main channel 204 that fluidly connects buffer reservoir 206 and waste reservoir 208. Main channel 204 is comprised, at least in part, of a separation channel portion or zone 210. As shown, the separation channel portion 210 has a serpentine geometry in order to maximize the separation achieved in the channel, i.e., increase the number of theoretical plates, while minimizing the amount of substrate area used. Injection channel 212 is in fluid communication with, e.g., intersects, main channel 204 at intersection 214. On one side of intersection 214, injection channel 212 is in fluid communication with four separate reservoirs 216, 218, 220 and 222. On the other side of intersection 214, the injection channel 212 terminates in waste reservoir 224. A detection window 226 is optionally provided in the body structure, disposed across the main channel 204 downstream from the separation channel portion 210 to permit the detection of materials separated therein. As noted, the device illustrated in FIG. 3 integrates the sources of the nested set of fragments within the same body structure that contains the separation channel.

In operation, buffer is placed in each of buffer well 206 and waste reservoirs 208 and 224. A first nested set of fragments of a target nucleic acid are placed in reservoir 216, while a second nested set is placed in reservoir 218. Optional third and fourth nested sets are placed in reservoirs 220 and 222, respectively. By way of example, the nested set of fragments of the target that terminate in the various adenosine nucleotides or nucleotide analogs (A) are placed in reservoir 216. Production of these nested sets is typically carried out by methods that are well known in the art, such as extension in the presence of dideoxynucleotides (Sanger et al., Proc. Nat'l Acad. Sci., 74:5463–5467 (1977)), or extension in the presence of boronated nucleotides (Porter et al., Nucleic Acids Res. 25(8)-1611–1617 (1997)), or separate, partial and selective cleavage at each of the four nucleotides (Maxam and Gilbert, Proc. Nat'l Acad. Sci., 74:560–564 (1977)). A second nested set, such as those fragments terminating in, or immediately adjacent to, the thymidine nucleotides in the target sequence, is placed in reservoir 218. A third nested set terminating in or immediately adjacent to all of the cytosine nucleotides is placed in reservoir 220 while the fragments terminating at or immediately adjacent to guanosine are placed in reservoir 222.

Utilizing controlled electrokinetic transport, a selected concentration of each nested set is transported from its respective reservoir (216, 218, 220, 222) into injection channel 212, across intersection 214, and toward waste reservoir 224. As described in greater detail above, this is accomplished by applying a voltage gradient between (1) each of reservoirs 216, 218, 220, 222 and (2) waste reservoir 224. As electrophoretic flow is related to current flow, one modulates or selects the relative concentration of the nested sets being transported from each of these reservoirs by modulating the percentage of the overall current flow originating from each of these reservoirs. For example, assuming that 10 $\mu$A of current is applied through injection channel 212, one attains a 70:10:10:10 ratio of each of the fragment populations within the injection channel, by applying 7 $\mu$A from reservoir 216 and 1 $\mu$A each from reservoirs 218, 220 and 222. The resulting concentration of nucleic acid fragments within the injection channel is 70% of the first nested set (terminating in A), and 10% of each of the second, third and fourth nested sets (terminating in T, G and C, respectively).

The mixture is transported across the intersection, typically in a pinched format, as described above, to prevent diffusional leakage into the separation channel. After sufficient time has elapsed to ensure that the mixture traversing the intersection is a homogenous mixture, i.e., has no electrophoretic biasing, etc., the pinched portion of the mixture at the intersection is then injected into the main channel 204, by switching the voltage gradient to between reservoirs 206 and 208. The injected mixture then moves into the main channel 204 and into the separation zone 210, whereupon the various fragments within the mixture are separated by size. Following their separation by size, the fragments are then detected at detection window 226. As each of the fragments is from the first or second nested set, separation of these fragments produces a ladder of separated molecules (or signal peaks) where each peak corresponds to a fragment having one additional nucleotide added to its terminus. The fragments that are present in higher concentration, e.g., those from the first nested set terminating in A, produce larger signal peaks than those from the remaining sets (e.g., those terminating in T, G or C). From the ladder and peak size differential, it can be readily determined which positions are occupied by the first selected nucleotide (A in the present example).

The relative positions of each of the other nucleotides is readily determined using the same method, but modulating the relative concentrations of the nested sets that are being transported across the injection intersection. In particular, the next nested set is transported into the injection channel at a higher concentration than each of the other sets, and this mixture is injected, separated, detected and the positions of the terminating base of that set are determined. This is again repeated with the remaining sets as needed. It bears noting that a fourth step may not be required if there s sufficient confidence in the separation and characterization of the first three sets, i.e., the positions occupied by the fourth selected nucleotide within the target sequence are determined by elimination.

Examples of signal plots from the above-described method are illustrated in FIG. 3A–3D. In particular, each of FIGS. 3A–3D illustrates a plot of relative fluorescence vs. time as detected at detection window 226. The peaks indicate the fragments that are eluting from the separation channel, e.g., passing by the detection window, with the smallest fragments eluting first. FIG. 3A illustrates the example described above, where the nested set of fragments that terminate in A, or its analog, is injected at a greater concentration than the remaining fragments. From the figure, it can be discerned that the base A occurs at relative positions 1, 3, 8, 9 and 11 in the target sequence. The separation is repeated, but where the second nested set or the set terminating in T, is mixed at a greater concentration than the remaining nucleotides. This mixture is injected, separated and detected as shown in FIG. 3B. From the results shown in FIG. 3B, it is determined that T occupies positions 2, 7, 10, 14 and 17. FIGS. 3C and 3D illustrate the injection separation and detection of the nested sets terminating in G and C, respectively. From the plots in FIG. 3C and 3D, it can be determined that G occupies positions 4, 13 and 15, while C occupies positions 5, 6, 12 and 16.

In practicing the methods of the invention, a first volume or concentration of the first nested set is mixed with a second, lesser volume or concentration of the second nested set. A representative fraction or portion of this mixture is then injected into the separation channel. Upon separation within the separation channel and detection, the different sized fragments of the first nested set will produce signal peaks corresponding to the molecular weight or size of the fragments. These signal peaks also have a first amplitude that corresponds to the fragments' concentration. The differently sized fragments in the second nested set also will produce signal peaks corresponding to their size, and having a smaller amplitude than the first set, again, corresponding to their concentration.

In order to ensure differentiation between the first and second nested sets upon separation and detection, the first set concentration will typically be greater than twice the second set concentration, preferably greater three times the second set concentration, more preferably, greater than 4 times the second set concentration, still more preferably, greater than five times the second concentration, and often greater than about ten times the second concentration.

The microfluidic devices described herein, are typically part of a larger microfluidic system that includes the devices coupled to a controller unit, e.g., an electrical controller, to direct and control material transport, to a detector to detect materials being transported through, e.g., separated in, the microfluidic device, and a computer or processor to instruct each of these components in their operation, e.g., instructing the electrical controller to deliver appropriate currents and voltages to appropriate ports of the device, and receiving, recording and aiding in the interpretation of the data from the detector.

Figure 4:
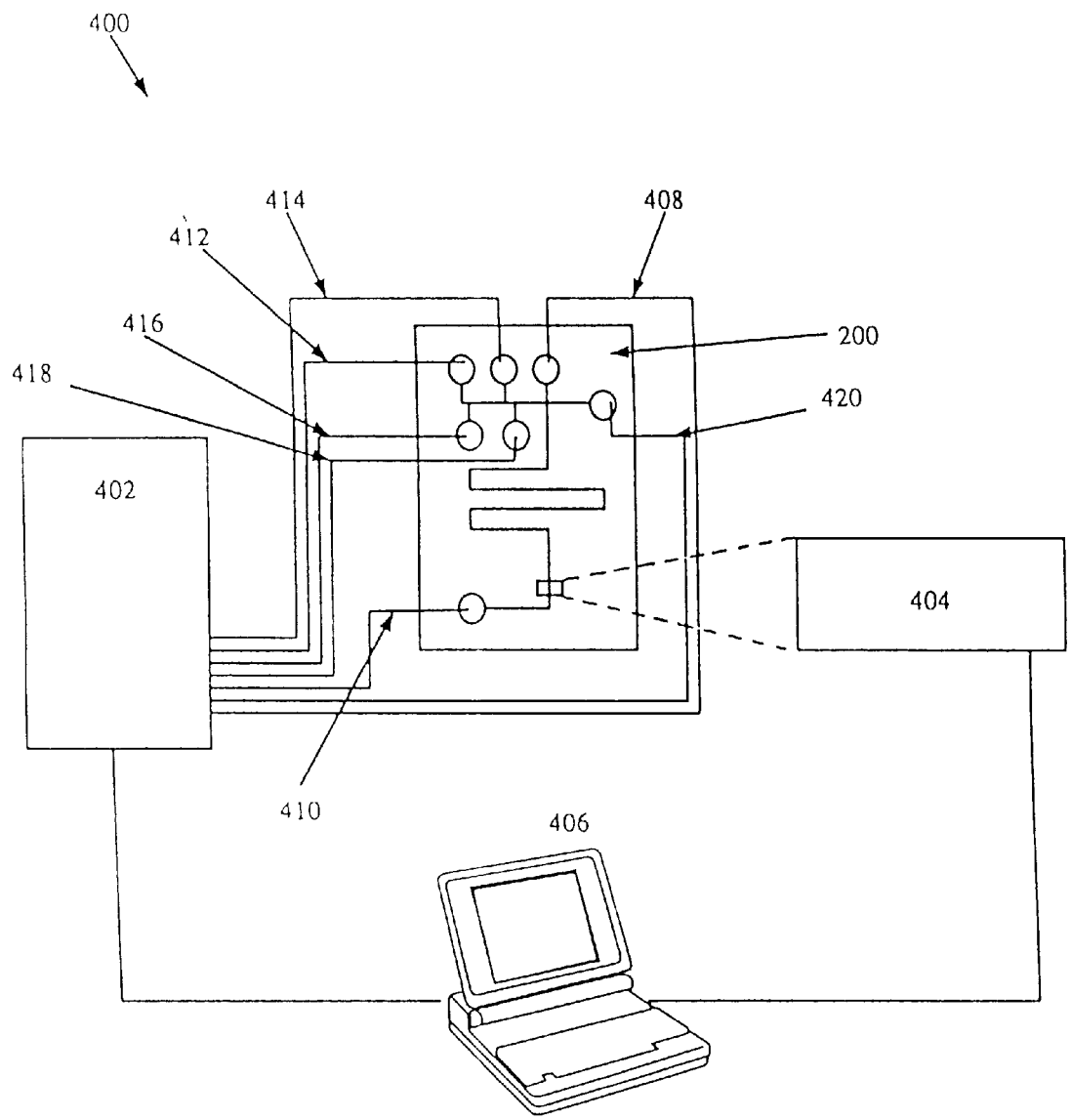
FIG. 4 schematically illustrates an overall microfluidic system for performing sequence analysis of target nucleic acids.

An example of an overall system incorporating the microfluidic devices described above, is illustrated in FIG. 4. As shown, the system 400 includes a microfluidic device 200 as shown in FIG. 2. The system also includes an electrical controller 402 and a detector 404, both of which are operably coupled to a processor or computer 406. The electrical controller 402 includes a plurality of electrical leads 408 through 420, each of which is in electrical connection with a separate one of reservoirs 206, 208, 216–224, respectively. The electrical controller operates by delivering separate voltages to each of the reservoirs via the separate leads, to produce appropriate voltage gradients to drive material transport, as described above.

In particularly preferred aspects, the electrical controller provides appropriate voltage gradients across the length of a channel by applying voltages to reservoirs at the termini of that channel, where the voltages are responsive to the amount of current flowing through a given channel. In particular, in electrokinetic material transport systems, the relative potentials at the intersections of the channels dictates the direction and velocity of material movement at those intersections. Control of these potentials has previously relied upon the calculation of applied voltages based upon the desired potential at the intersections, and the resistance of the channel between the intersection and the electrodes at which voltages are applied. By monitoring and controlling the current, the potential at the intersection is maintained at the desired level, and the applied voltages are self-regulating. Examples of preferred electrical controllers are described in, e.g., International Patent Application No. PCT/US97/12930, and U.S. Ser. No. 888,064, both of which were filed Jul. 3, 1997, and are incorporated herein by reference in their entirety, for all purposes.

In terms of the device shown in FIG. 2, the controller controls or supplies the voltage applied at the buffer reservoir 206, waste reservoirs 208 and 224, and the nested set source reservoirs 216, 218, 220 and 222. Applied voltages are modulated, as described above, to selectively mix different amounts of each of the nested sets in the injection channel 212, and then to inject a portion of the mixture into the separation portion 210 of the main channel 204.

Detector 404 is operably coupled to computer 406, and is disposed within sensory communication of the main channel 204 of the device 202. "In sensory communication" as used herein, means that the detector is capable of receiving a detectable signal from the main channel 204. In particular, detection of nucleic acid fragments in accordance with the present invention typically utilizes a labeling group bound or otherwise associated with the nucleic acid fragment. This labeling group then permits the detection of the fragment via transmission of the signal from the label group through the detection window, where that signal is received by the detector, and typically transmitted to a computer for recording. A variety of labeling groups may be employed in accordance with the present invention, including both directly and indirectly associated labeling groups. A variety of well known labeling techniques are used in labeling the nucleic acid fragments described herein. For example, in preferred aspects, optical labels, such as fluorogenic or fluorescent groups, chromophoric or chromogenic groups, colloidal labels and the like are used in labeling the nucleic acid fragments. However, other labeling systems are also useful in accordance with these methods, including radiolabels, labeling with one member of a specific binding pair, e.g., biotin, avidin or streptavidin.

In particularly preferred aspects, the nucleic acid fragments are labeled with a fluorescent moiety, e.g., fluorescein, rhodamine or derivatives thereof. Examples of nucleotides that incorporate such fluorescent moieties are described in, e.g., U.S. Pat. Nos. 4,711,955, 5,171,534, 5,187,085, 5,188,934, and 5,366,860. In this embodiment, the detector is disposed in optical communication with the main channel 204, and preferably adjacent to the detection window 226. Further, in the case of fluorescently labeled nucleic acid fragments, the detector will also include a source of activation light directed at the main channel 204, through the detection window. The activation light typically produces light at a sufficient wavelength to activate the fluorescent group, whereupon the fluorescent group emits light at a characteristic wavelength, typically different from that of the activation light. Because the system and methods of the present invention rely upon the concentration differences between different nested sets of fragments of the target nucleic acid sequence, it is possible, and even preferable to use single color detection optics, e.g., a single type of fluorescent label, excited with a single light source and detected at substantially a single wavelength. Specifically, by employing only a single fluorescent label group, the system described herein can employ an excitation light source that is optimized for that label. This is in contrast to multi-color detection schemes where a single excitation light source must produce light which overlaps the excitation spectra of all of the labels used. The result in the case of the present invention is to permit fluorescent excitation and detection at much higher efficiencies, e.g., higher quantum fluorescence yields.

The detector also typically includes focusing and separation optics for accurately directing the activation light through the detection window, and for collecting emitted fluorescence as well as reflected excitation light. These optics also typically separate the reflected excitation light from the emitted fluorescence, through the incorporation of a dichroic mirror, thereby permitting detection of only the fluorescent emission. Ultimate detection is typically accomplished via an incorporated photomultiplier tube or photodiode. A variety of additional optical treatments may be employed in the detector to optimize the detection operation, including incorporation of confocal optics, autofocus systems and the like.

The detector is coupled to the computer, wherein the light detected from the main channel is recorded as a function of the retention time within the separation channel. The computer 406 is typically appropriately programmed to record and store the data received from the detector. The computer is also typically programmed to instruct the electrical controller to deliver appropriate current through the various electrical leads, and to the reservoirs of the microfluidic system, in accordance with the operator's instructions.

Figure 5:
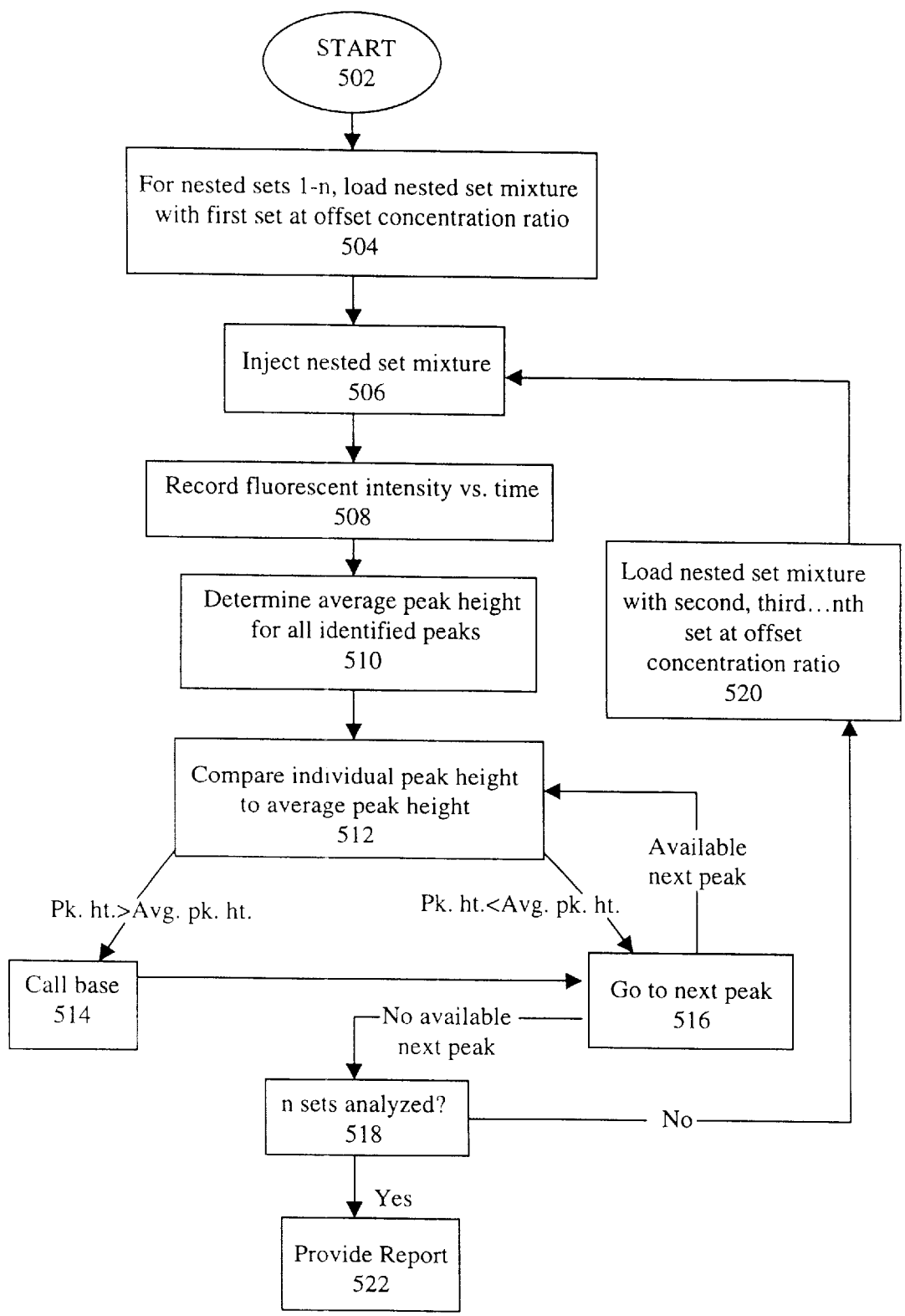
FIG. 5 illustrates one example of a process or software program for identifying nucleotides that occupy given positions within a target nucleic acid sequence.

FIG. 5 schematically illustrates exemplary process steps carried out by the computer or processor in accordance with its programming. As shown, and with reference to the device of FIG. 2 and the system of FIG. 4, the computer 406 begins the operation at step 502, typically at the initiation of the user or operator. At step 504, the computer instructs the electrical controller to deliver the appropriate currents to the ports of the microfluidic device (206, 208, 216–224) so that appropriate concentrations of each of the nested sets are transported or loaded into injection channel 212 and across intersection 214 toward waste reservoir 224. Specifically, a selected nested set, i.e., a first nested set terminating in a selected nucleotide, is loaded at an offset, and typically higher concentration. At step 506, the computer instructs the electrical controller to change the applied voltages to inject that portion of the mixture within intersection 214, into main channel 204, typically with appropriate pinching flows from the side channels, as described above. At step 508, the computer 406 receives the data from the detector 404, which is located in sensory communication with main channel 204 via detection window 226, and records fluorescent intensity as a function of the amount of elapsed time since the beginning of the operation. This progresses for a preselected time period, typically determined based upon the maximum expected time for all relevant species to travel through the separation channel portion and past the detection window.

At step 510, the computer begins analyzing the recorded data to differentiate between fragments from the first nested set and all other fragments. For example, as shown, at step 510, the computer determines the average peak height for all identified peaks in the plot of fluorescence. The computer, at step 512, then selects one peak, i.e., the first eluted peak, identified according to its position relative to the other peaks, and compares the height of the selected peak to the average peak height. If the peak height is greater than the average peak height by a preset margin, e.g., 1.5X, 2X, 3X, 4X, 5X or the like, then at step 514, the computer identifies that peak as corresponding to the selected base for that relative position in the sequence, or calls the base. If the peak height is less than the average peak height, i.e., by the above-described preset margin, then the computer identifies that peak as not corresponding to the selected base for that relative position, and moves on to step 516.

Whether the peak is identified as the selected base or not, the computer at step 516, then moves on to the next, different peak, i.e., the next peak to elute, and repeats steps 512 through 516. Once the computer analyzes each separate peak, i.e., has no additional peaks to analyze, then at step 518, the computer optionally determines whether all of the nested sets have been analyzed, e.g., in the case of sequencing operations. If all sets have not been analyzed, at step 520, the computer begins loading the next nested set mixture in the same fashion as the first, e.g., by applying appropriate voltages to the various reservoirs of the device. The next nested set is loaded such that a different nested set is loaded at an offset or different concentration than the other sets. Steps 506 through 520 are then repeated until all of the nested sets have been analyzed. In the case of sequencing operations, this typically includes four different nested sets, where the fragments in each different nested set terminate in a different nucleotide, e.g., dideoxynucleotide or boronated nucleotide.

If all n nested sets have been analyzed, at step 522, the computer provides a report on the relative positions occupied by the selected nucleotides from each nested set analyzed. In the case where all four nested sets of nucleotide fragments are analyzed, this report will basically provide the nucleotide sequence of the target nucleic acid. Optionally, at step 518 the computer instructs the electrical controller to load a further mixture of nested sets, e.g., where the next selected nested set, e.g., the second, third, fourth . . . nth, is loaded at a higher concentration than the remaining sets. Specifically, a second, third . . . or nth, nested set, e.g., terminating in a second, third . . . or nth nucleotide, is loaded at a higher concentration than the other nested sets of nucleic acid fragments. The overall process is then performed, on the new mixture of nested sets. This is repeated for each of the remaining nested sets of nucleic acid fragments. As noted, this is typically repeated for each of the four different nucleotides that terminate the various nested sets. However, different concentrations of each nested set can be provided in each run, to minimize the number of process runs required to determine the entire sequence. After all n sets have been analyzed, then the computer proceeds to step 520 and provides the report of relative base positions.

Although the present invention has been described in some detail by way of illustration and example for purposes of clarity and understanding, it will be apparent that certain changes and modifications may be practiced within the scope of the appended claims. All publications, patents and patent applications referenced herein are hereby incorporated by reference in their entirety for all purposes as if each such publication, patent or patent application had been individually indicated to be incorporated by reference.

What is claimed is:

1. A method of mixing and separating nucleic acids, the method comprising:

mixing a plurality of sets of nested nucleic acid fragments in a mixing channel;

flowing the resulting nucleic acid fragment mixture to a fluidly coupled separated channel comprising a separation matrix; and, separating the nucleic acid fragment mixture by flowing the mixture through the separation channel, thereby providing separated nucleic acid fragments.

2. The method of claim 1, further comprising providing a plurality of source of the nested nucleic acid fragments, thereby providing the plurality of sets of nested nucleic acid fragments which are mixed in the mixing channel.

3. The method of claim 2, wherein the plurality of sources are fluidly coupled to the mixing channel, the method further comprising flowing the plurality of sets of nested nucleic acid fragments from the plurality of sources into the mixing channel.

4. The method of claim 1, wherein each of the sets of nested nucleic acid fragments are provided by performing a plurality of dideoxy chain termination reactions using a selected target nucleic acid as a template.

5. The method of claim 4, wherein each of the plurality of dideoxy chain reactions comprises a different dideoxy chain termination nucleotide.

6. The method of claim 1, wherein each of the sets of nested nucleic acid fragments are provided by performing an extension reaction in the presence of boronated nucleotides, using a target nucleic acid as a template.

7. The method of claim 6, wherein each of the plurality of extension reactions comprises a different boronated nucleotide.

8. The method of claim 1, wherein each of the sets of nested nucleic acid fragments are provided by performing a dideoxy chain termination reaction using a target nucleic acid as a template, or by performing an extension reaction in the presence of boronated nucleotides using the target nucleic acid as a template, wherein each of the sets of nested nucleic acid fragments comprise a first label, wherein the first label is the same for each of the sets of nested nucleic acid fragments.

9. The method of claim 1, wherein each of the sets of nested nucleic acid fragments comprise a first label, wherein the first label is the same for each of the sets of nested nucleic fragments.

10. The method of claim 1, comprising mixing the plurality of sets of nested fragments at detectably different concentrations to provide the mixture.

11. The method of claim 1, further comprising detecting the separated nucleic acid fragments.

12. The method of claim 1, wherein the plurality of sets of nested nucleic acid fragments are made by performing one or more sequencing reaction using a target nucleic acid as a template.

13. The method of claim 12, further comprising determining the sequence of the target nucleic acid by detecting the separated nucleic acid fragments.

14. The method of claim 1, further comprising detecting the separated nucleic acid fragments, thereby providing signals corresponding to the detected nucleic acid fragments and recording the presence of the signals.

15. The method of claim 14, further comprising analyzing the resulting recorded signal to distinguish between different sets of nucleic acid fragments in the plurality of sets of nucleic acid fragments.

16. The method of claim 15, wherein the analyzing step comprises determining an average peak height for a plurality of the signals.

17. The method of claim 15, wherein the analyzing step comprises determining an average peak height for a plurality of the signals and determining the relative position of a plurality of the plurality of signals.

18. The method of claim 17, wherein the sets of nested nucleic acid fragments correspond to a sequence of a target nucleic acid, the method further comprising converting the average peak height and relative position for the plurality or a plurality of signals into a nucleic sequence corresponding to the sequence of the target nucleic acid.

19. The method of claim 15, wherein the analyzing step is performed using a computer.

20. The method of claim 19, wherein the computer reports the relative position of the signals.

21. The method of claim 1, wherein the nucleic acid fragment mixture is flowing to the fluidly coupled separation channel using an electrokinetic material transport system.

22. The method of claim 1, wherein the nucleic acid fragment mixture is flowed to the fluidly coupled separation channel using an electrokinetic material transport system, wherein the mixture is introduced from the mixing channel into the separation channel by performing a pinched injection.

23. The method of claim 1, wherein the separation matrix comprises one or more of: an acrylamide polymer, a methylacrylamide polymer, a dimethylacrylamide polymer, hydroxymethyl cellulose, and agarose.

24. The method of claim 1, further comprising providing a body structure comprising the separation and mixing channels.

25. The method of claim 24, wherein the body structure is fabricated from one or more of: a polymer, glass, and quartz.

26. The method of claim 24, wherein the body structure is provided by fabricating channels in a first substrate corresponding to the separation and mixing channels and covering the first substrate with a cover layer.

* * * * *

UNITED STATES PATENT AND TRADEMARK OFFICE
CERTIFICATE OF CORRECTION

PATENT NO : 6,107,044
DATED : August 22, 2000
INVENTOR(S) : Nikiforov

It is certified that error appears in the above-identified patent and that said Letters Patent are hereby corrected as shown below:

Claim 1, line 6, after "coupled", please delete "separated" and insert --separation--.

Claim 2, line 2, after "plurality of", please delete "source" and insert --sources of the sets--.

Claim 21, line 2, after "mixture is", please delete "flowing" and insert --flowed--.

Signed and Sealed this

Twenty-fourth Day of April, 2001

NICHOLAS P. GODICI

Attest:

Attesting Officer

Acting Director of the United States Patent and Trademark Office